(12) United States Patent
Wong et al.

(10) Patent No.: US 10,022,502 B2
(45) Date of Patent: Jul. 17, 2018

(54) DOSE GUIDES FOR INJECTION SYRINGE

(75) Inventors: Vernon G. Wong, Menlo Park, CA (US); Tan Pham, San Jose, CA (US); William S. White, Birmingham, AL (US); Glenn T. Huang, Fremont, CA (US); Mae W. Hu, Los Altos Hills, CA (US)

(73) Assignee: ICON BIOSCIENCE, INC., Sunnyvale, CA (US)

( * ) Notice: Subject to any disclaimer, the term of this patent is extended or adjusted under 35 U.S.C. 154(b) by 788 days.

(21) Appl. No.: 14/113,803

(22) PCT Filed: Apr. 25, 2012

(86) PCT No.: PCT/US2012/035028
§ 371 (c)(1),
(2), (4) Date: Dec. 17, 2013

(87) PCT Pub. No.: WO2012/149040
PCT Pub. Date: Nov. 1, 2012

(65) Prior Publication Data
US 2014/0180245 A1 Jun. 26, 2014

Related U.S. Application Data

(60) Provisional application No. 61/478,748, filed on Apr. 25, 2011, provisional application No. 61/597,248, filed on Feb. 10, 2012.

(51) Int. Cl.
*A61M 5/315* (2006.01)

(52) U.S. Cl.
CPC ........ *A61M 5/31536* (2013.01); *A61M 5/315* (2013.01); *A61M 5/3156* (2013.01); *A61M 5/31591* (2013.01)

(58) Field of Classification Search
CPC ............ A61M 5/3146; A61M 5/31536; A61M 5/3156; A61M 5/31591; A61M 5/31593; A61M 5/31595
See application file for complete search history.

(56) References Cited

U.S. PATENT DOCUMENTS 3,770,026 A * 11/1973 Isenberg ........... A61M 5/31525
141/2
4,246,898 A 1/1981 Travalent et al.
4,874,385 A 10/1989 Moran et al.
(Continued)

FOREIGN PATENT DOCUMENTS

DE 3410336 A1 5/1985
DE 3509865 A1 9/1986
(Continued)

OTHER PUBLICATIONS

Extended European Search Report, dated Aug. 25, 2014, cited in related EP Application No. 12776388.6, filed Apr. 25, 2012.
(Continued)

*Primary Examiner* — Nathan R Price
*Assistant Examiner* — Justin L Zamory
(74) *Attorney, Agent, or Firm* — Medler Ferro Woodhouse & Mills PLLC (57) ABSTRACT

Devices that guide the accurate loading and dispensing of predetermined doses of fluid from injection syringes are disclosed.

9 Claims, 6 Drawing Sheets

(56) References Cited

U.S. PATENT DOCUMENTS

| | | | | |
|---|---|---|---|---|
| 5,833,669 A | * | 11/1998 | Wyrick | ............. A61M 5/31511 |
| | | | | 604/208 |
| 5,975,355 A | | 11/1999 | Cecala et al. | |
| 2003/0225358 A1 | | 12/2003 | Berman et al. | |
| 2005/0008683 A1 | * | 1/2005 | Mikszta | ................ A61K 38/21 |
| | | | | 424/448 |
| 2016/0120879 A1 | | 5/2016 | Wong et al. | |

FOREIGN PATENT DOCUMENTS

| | | |
|---|---|---|
| DE | 202009011284 U1 | 4/2010 |
| EP | 1559443 A1 | 8/2005 |
| EP | 1702636 A1 | 9/2006 |
| WO | 2007-042592 A1 | 4/2007 |
| WO | 2009-095735 A1 | 8/2009 |
| WO | 2014/190248 A1 | 11/2014 |

OTHER PUBLICATIONS

International Search Report and Written Opinion in PCT/US2012/035028, dated Nov. 28, 2012.

\* cited by examiner

DOSE GUIDES FOR INJECTION SYRINGE

RELATED APPLICATIONS

The present application is a National Stage of International patent application PCT/US2012/035028, filed on Apr. 25, 2012, which claims the benefit of U.S. Patent Applications No. 61/478,748, filed Apr. 25, 2011, and No. 61/597,248, filed Feb. 10, 2012, each of which is incorporated fully herein by reference.

BACKGROUND

A hypodermic syringe is an important piece of medical equipment for many individuals ranging from surgeons to patients. With advancements in modern medicine, shorter needles, longer reservoirs, and virtually painless injections, syringes have changed for the better. Nevertheless, it remains difficult for even skilled practitioners to load a syringe with precise volumes and administer the unit volume (e.g., dose) accurately. This is particularly important for injections where variations can result in adverse clinical effects, such as highly potent medicines (e.g., insulin), in certain settings where small doses are administered (e.g., intraocular injections), or where the care giver is less skilled or has difficulty handling the syringe loading process. There is a need in the art for simple yet accurate means for loading and delivering more accurate volumes using standard syringes.

SUMMARY

The present invention provides for a system comprising at least one device that allows for accurate loading and/or delivery of precise volumes of fluid (e.g., sample or medicament) using a standard injection syringe.

In some aspects of the invention, the system comprises a removable dose-loading "spacer" guide of predetermined dimensions that, in use, is placed abutting the end of a standard syringe where the plunger extends from the syringe barrel (typically placed slidably adjacent to the plunger) that is loaded with an excess of fluid (e.g., medicine), from which the excess fluid is then expelled as regulated by the spacer guide to provide for an accurate loading of fluid volume (e.g., unit dose) within the syringe. The dose-loading spacer is then removed from the syringe/plunger junction, and the remaining volume (dose) can be delivered from the syringe.

In other aspects, the system comprises a dose-delivery guide of predetermined dimensions, used to deliver an accurate dose to the subject. In use, the dose-delivery guide is placed abutting the top of the barrel of a syringe (i.e., where the plunger extends from the barrel) either before or after the syringe has been loaded with fluid, then the fluid (e.g., dose of medicine) is delivered to the subject by depression of the plunger, wherein the dose-delivery guide regulates the delivery of the dose volume by stopping the motion of the plunger according to the predetermined parameters of the dose-delivery guide. In a particular aspect, the dose-delivery guide is integral to the proximal end of the plunger rod.

In another aspect, the dose-loading spacer and the dose-delivery guide are used synergistically to provide for an accurate delivery of the dose. The dose-loading spacer defines the volume of the fluid prior to administration and the dose-delivery guide assures a more accurate delivery of the dose. The dose-delivery guide may be positioned before or after the syringe has been filled with fluid (e.g., medicine); or before or after the dose-loading spacer has been used. If the dose-delivery guide is in place at the top of the syringes barrel, the dose-loading spacer is positioned either over the dose-delivery guide (i.e., encompassing the guide) or adjacent to the dose-delivery guide (e.g., abutting the guide and the plunger), depending on the predetermined parameters of the dose-loading spacer, typically but not necessarily after the syringe has been filled with an excess of fluid. The excess fluid expelled according to the spacer to provide an accurate dose loaded in the syringe; then the dose loading spacer is removed but the dose-delivery guide is left in place, such that the remaining fluid (dose) is delivered to the subject by depression of the plunger, wherein the dose-delivery guide regulates the delivery of the dose volume by stopping the motion of the plunger according to the predetermined parameters of the dose-delivery guide. In a specific embodiment, the dose-delivery guide is integral to the plunger for use with a standard glass syringe such as BD 0.5 cc Hypak™ glass syringe.

Using the system of the dose-loading spacer and, optionally, the dose-delivery guide is relatively easy, such that elderly patients or children of appropriate age (e.g., diabetics who inject insulin at home), can achieve precise dosing easily and accurately.

A particular aspect of the invention is a dose-loading "spacer" guide for loading an injection syringe, the spacer having a grip portion and a collar portion, the collar portion configured to be placed at the proximal (top) end of a syringe barrel, slidably abutting an extended syringe plunger rod; wherein the collar is rigid and includes an opening for receiving the extended syringe plunger, and an inner wall that bears against the plunger rod for guided displacement therealong, and wherein the collar has predetermined dimensions and, in use, stops the movement of the plunger toward the syringe barrel at a predetermined distance from the syringe barrel, which distance is directly related to the volume to be loaded in the injection syringe.

Another particular aspect of the invention is a dose-delivery guide for controlling the volume expelled from a loaded injection syringe, the dose-delivery guide configured to be at the proximal (top) end of a syringe barrel, slidably abutting an extended syringe plunger rod; wherein the dose-delivery guide is rigid in length and includes an opening for receiving the extended syringe plunger rod, which opening allows the plunger to move freely through the guide until motion of the plunger is impeded by the guide, wherein the dose-delivery guide has predetermined dimensions and a rigid height that, in use, stops the movement of the plunger toward the syringe barrel at a predetermined distance from the syringe barrel, which distance is related to the volume (dose) to be delivered by the injection syringe. The dose-delivery guide can have a continuous circumference for placement onto a syringe plunger before the plunger is engaged with the syringe, or can have a discontinuous circumference for placement onto a plunger that is already engaged with the syringe. The dose-delivery guide may be integral to the plunger rod. In a specific embodiment, the dose-delivery guide is integral to the plunger for use with a standard glass syringe such as BD 0.5 cc Hypak™ glass syringe.

Another aspect of the invention is a dose-loading dose-delivery system comprising both a dose-loading "spacer" guide and a dose-delivery guide for loading and expelling the volume (dose) of a syringe. In use, for example, the dose-delivery guide is placed at the top (proximal end) of the syringe barrel, typically steadied against the plunger rod, either before or after the plunger is engaged with the syringe;

excess fluid is loaded into the syringe or the syringe may have been preloaded with excess fluid; the dose-loading spacer is placed over, or adjacent to, the dose-delivery guide, and excess fluid is expelled from the syringe as determined by the dose-loading spacer (i.e., the plunger is depressed until its motion is stopped by the dose-loading spacer) and the dose-loading spacer is removed; remaining fluid in the syringe is then delivered to the subject by depressing the plunger until the plunger's motion is stopped by the dose-delivery guide.

Alternatively, the invention is a dose-loading dose-delivery system comprises a removable dose-loading "spacer" guide and a dose-delivery guide integral to the plunger rod for loading and expelling the volume (dose) of a syringe. In use, for example, the syringe has been preloaded or is loaded with excess fluid; the dose-loading spacer is placed over, or adjacent to, the dose-delivery guide; excess fluid is expelled from the syringe as determined by the dose-loading spacer (i.e., the plunger is depressed until its motion is stopped by the dose-loading spacer); the dose-loading spacer is removed; remaining fluid in the syringe is then delivered to the subject by depressing the plunger until the plunger's motion is stopped by the dose-delivery guide.

DESCRIPTION OF THE DRAWINGS

In FIG. 3A, the syringe has been loaded with an excess volume of fluid; double arrow indicates the movement of the spacer into position. In FIG. 3B, the syringe guide has been placed at the proximal (top) end of the syringe barrel, abutting the plunger rod; double arrow indicates motion of the plunger. In FIG. 3C, the plunger has been depressed against the dose-loading spacer, which has regulated the expulsion of the excess fluid but caused the syringe to retain an accurate and pre-determined amount of fluid. In FIG. 3D, the guide has been removed, and the syringe contains the accurate dose as determined by the guide. The devices in the drawings of FIG. 3 are not to scale.

DETAILED DESCRIPTION

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. The term "or" is inclusive unless modified, for example, by "either." Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

An embodiment of the present invention provides for a dose-loading "spacer" guide for loading the correct volume of fluid (e.g., unit dose) in a standard hypodermic syringe. The term dose-loading spacer is synonymous with dose-loading guide, but in some instances herein, "spacer" is used to further distinguish from the dose-delivery guide described herein. The dose-loading spacer may be made of any suitably rigid material, such as plastic or metal (including recycled materials) that can be sterilized or otherwise cleaned for use. It may be removable or permanent in nature. The dose-loading guide may be reusable and long-lasting, or it may be disposable for single-use.

Figure 1A:
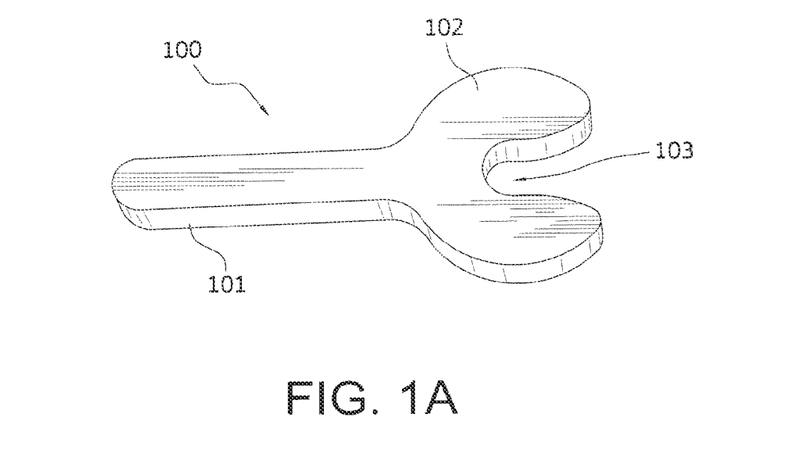
FIG. 1A is a photograph showing the top view of an embodiment of the invention.
Figure 1B:
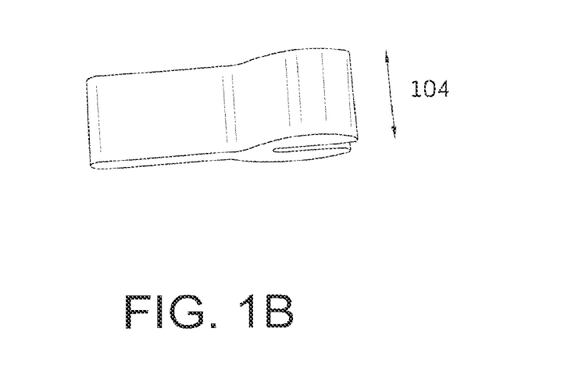
FIG. 1B shows a side view of an embodiment of the invention.

The dimensions of the spacer, particularly the height of the interior wall of the collar portion, for example as shown as (104) of FIG. 1, are designed in relation to the volume of the syringe to be used in conjunction with the guide. This relationship can be expressed as:

$$v = \pi r^2 h$$

where "v" is the unit volume μL (or cubic mm) to be delivered by the syringe; "r" is the mm radius of the interior of the syringe cylinder; and "h" is the mm length that the plunger has to travel to deliver the unit volume. For example, in a Becton Dickenson 28 gauge insulin syringe (product no. 309300), r=1.475 mm (one-half of the diameter of 2.95 mm). In this syringe, every 1 mm in length corresponds to 6.83 μL volume. If the unit volume to be delivered is 7.5 μL, (i.e., v=7.5); a spacer having a collar height of 1.1 mm (i.e. h=1.1 mm) can be used to measure a 7.5 μL dose (i.e., 7.514=(3.14)(1.475)²(1.1). Thus, one skilled in the art can use the volume dose and diameter of a given syringe to design the corresponding collar dimension. In a particular embodiment, a guide having a 1.1 mm collar is used to accurately load a 7.5 μL dose.

The handle portion of the spacer may be of any practical design (e.g., shape or texture) that allows the user to grip the guide for placement on (and, optionally, removal from) the syringe, e.g., on the top of the syringe barrel abutting the plunger rod. The handle portion may be manufactured contiguous to the collar, or may be connected (either detachably or fixed) to the collar portion by any other approach. The dose-loading guide may also bear a label or instruction(s).

As noted, the dose-loading guide of the present invention may be used with commercially available syringes. Because the spacer is useful for accurately loading small volumes, typically the syringe used will be for small-dose administration, such as a tuberculin syringe (Becton Dickinson, Franklin Lakes, N.J.) or an insulin syringe (Becton Dickinson), for example, BD 3/10 cc Insulin Syringe, or BD 0.5 cc Hypak™ glass syringe. The present dose-loading guide can also be used in other applications where accurate and repeatable volumes are required, for example syringes used to load chromatography samples such as HPLC or autosampler syringes (e.g., Hamilton Syringes, Sigma Aldrich, St. Louis, Mo.).

In use, the hypodermic syringe is loaded with fluid (e.g., medicine, drug, formulation, therapeutic agent, placebo, or sample) in excess of the amount needed for the actual dose. Air bubbles may be tapped out of the syringe and needle. The dose-loading guide is then placed on the proximal (top) end of the syringe barrel, abutting the plunger rod (typically where the plunger enters the syringe barrel), and the plunger depressed until the collar portion of the spacer stops the motion of the plunger. In this process, excess fluid is expelled from the syringe, leaving an accurate dose loaded in the barrel of the syringe as determined by the size of the collar portion of the dose-loading spacer. The guide may then removed, such that the plunger may be depressed fully as the dose is delivered. For example, a dose-loading guide can be used to accurately load 7.5 µL using a standard, commercially available tuberculin syringe.

Figure 2A:
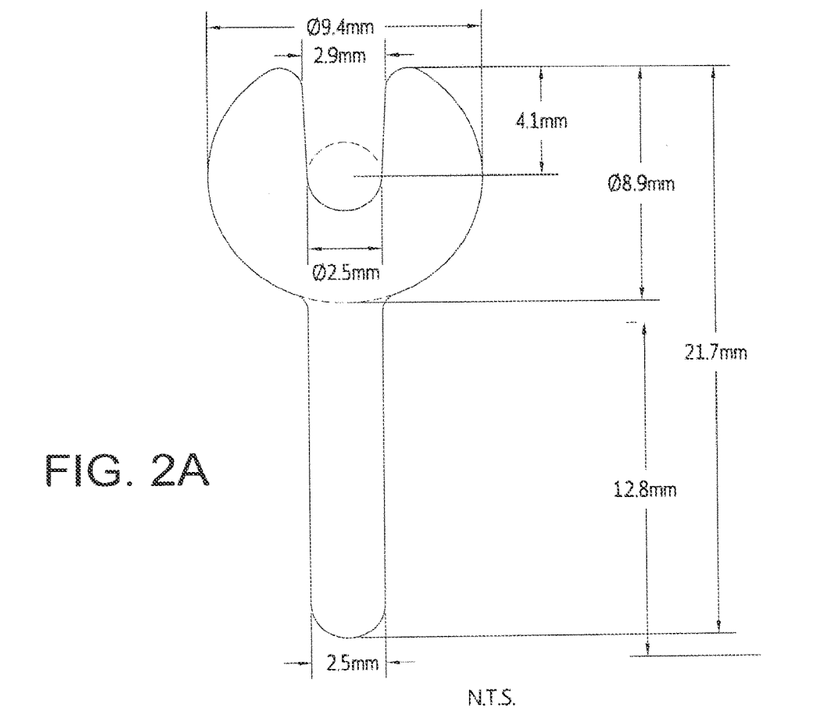
FIGS. 2A and 2B are schematic diagrams showing dimensions of an embodiment of the invention. "N.T.S." indicates drawings are not to scale.
Figure 2B:
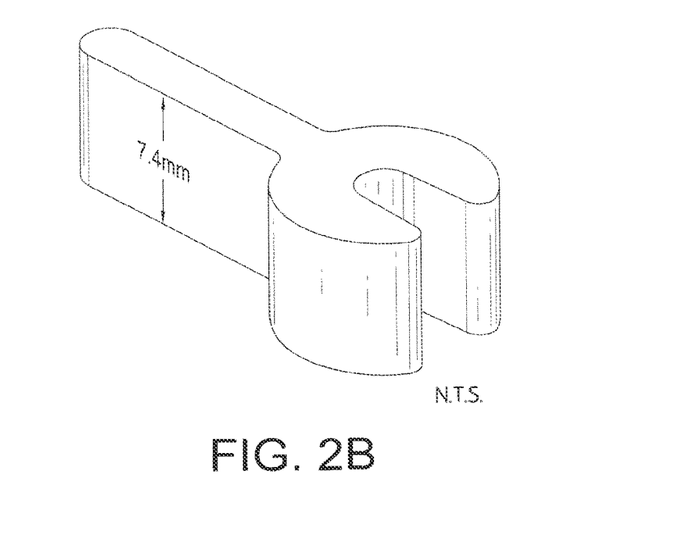
Figure 3A:
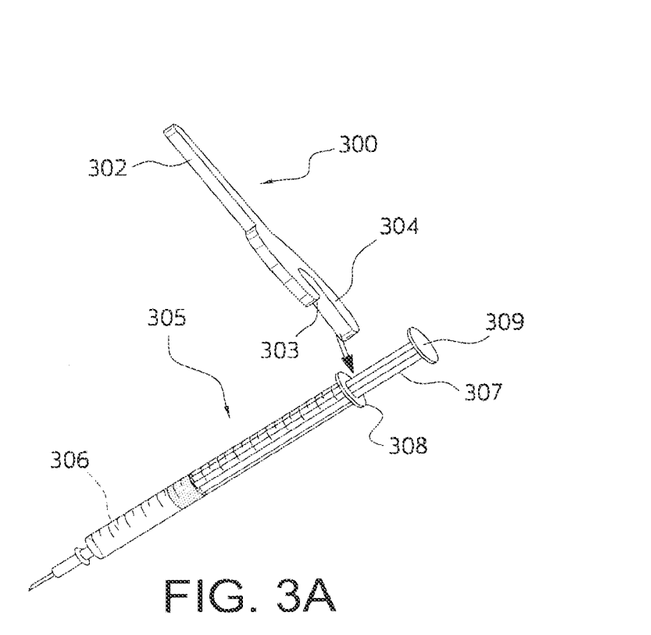
FIGS. 3A and 3D illustrate use of an embodiment of the dose-loading spacer with a conventional syringe.
Figure 3B:
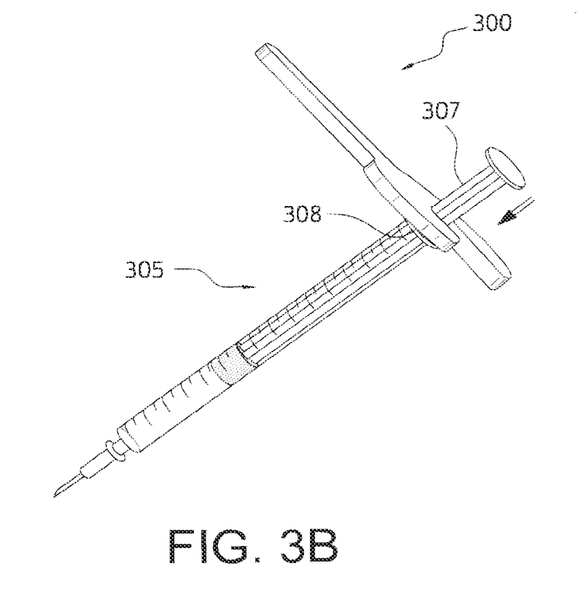
Figure 3C:
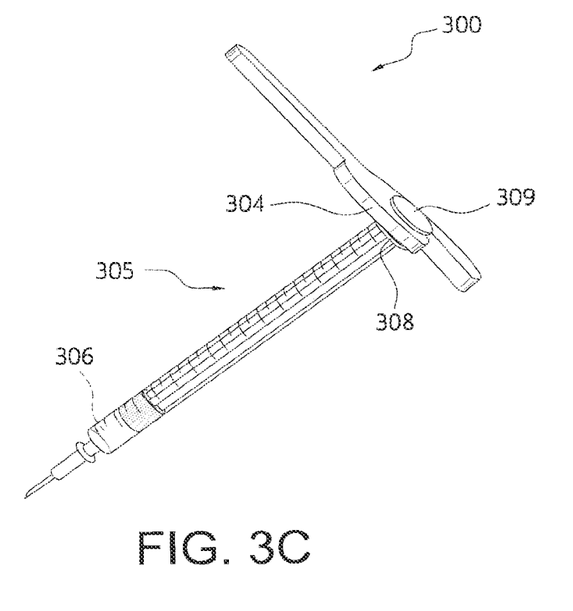
Figure 3D:
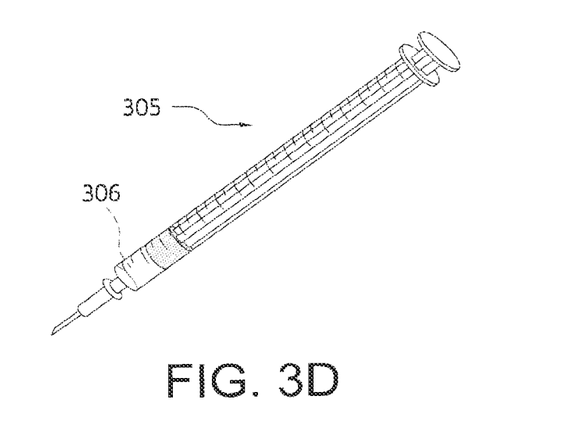

Referring to the Drawings, FIG. 1 shows an embodiment of the syringe dose-loading guide/spacer (100). The spacer has a grip portion (101) that serves as a handle or other means whereby the user can position the guide. The guide has a collar portion (102) that defines an opening (103) that is, in use, placed by the user such that it abuts the top end of a standard syringe. In use, the movement of the plunger rod into the barrel of the syringe is impeded by the height of the spacer (104). FIG. 2 presents measurements of particular parts of a dose-loading spacer embodiment.

Referring to FIG. 3, a standard, commercially available syringe (305) is loaded with formulation for injection (306), in an amount in excess of the desired dose. The guide (300) may be held by the grip portion (301) such that the collar portion (302) opening (303) abuts the proximal end of the syringe barrel (308), e.g., at the distal end of the extended syringe plunger rod (307). As indicated by the double arrow in FIG. 3B, the plunger (307) is then depressed into the barrel of the syringe (305) until the proximal end of the plunger (309) contacts the guide (300), as shown in FIG. 3C. Thus, the dose remaining in the syringe (306) is regulated directly by the dimension of the guide (304). Then, the guide may be removed, as shown in FIG. 3D, and the syringe is ready for the delivery (e.g., administration) of the accurately loaded dose.

Another aspect of the invention provides for a dose-delivery guide that can used without or in conjunction with a dose-loading guide to accurately deliver small volumes of fluid (e.g., medicament, pharmaceutical composition, sample, etc.) to a target (e.g., a subject or device). The dose-delivery guide has predetermined dimensions, designed to fit at the top (proximal) end of a standard syringe or integral to the plunger rod. The guide is optimally designed to remain stably in place on the syringe during use and does not have to be held in place by the user as the syringe is being used to deliver the dose. For example, the guide may be shaped to fit along and substantially around a syringe plunger rod and allow the plunger rod to move through the guide, or the guide may be integral to the plunger rod. This configuration allows the user to inject the syringe with one hand holding the syringe and the other hand free for any particular use. The circumference of the dose-delivery guide may be deformable or rigid, continuous or non-continuous, such that it may be placed abutting the syringe plunger either before or after the plunger is engaged with its syringe, respectively. The guide may be removable or permanent. The guide may be configured to be placed on the syringe either before or after the syringe is loaded. The dose-delivery guide must maintain rigidity along its height (i.e., the dimension related to the dose volume). The dose-delivery guide may be made of any suitable material, e.g., metal or sterilizable plastic, which maintains dimension along the length of the guide.

The use of the dual dose-loading and dose-delivery system is advantageous where syringe devices have deformable plunger/syringe interfaces, such as rubber ends, where the pressure exerted by the user can lead to a larger volume being delivered than is intended. Because the distance the plunger travels within the syringe barrel is fixed by the height of the dose-loading spacer and the height of the dose-delivery guide (rather than the depression of the plunger against the syringe), a more precise and accurate volume of medication can be administered. The difference in the dimensions of the height of the dose-loading spacer and the height of the dose-delivery guide are calculated from the formula:

$$V=\pi r^2 h$$

where V is the volume delivered, r is the radius of the inner dimension of the syringe barrel and h is the distance the piston has to travel along the length of the syringe barrel. For example, if the dose volume to be delivered is 7.5 µL, then:

$$V=7.5 \text{ µL or } 7.5 \text{ mm}^3$$

$$r=2.3 \text{ mm (diameter was measured to be 4.6 mm)}$$

$$V=\pi r^2 h, \text{ or } h=V/\pi r^2$$

$$h=7.5 \text{ mm}^3/(3.14)(2.3 \text{ mm})(2.3 \text{ mm})=0.45 \text{ mm}$$

Thus, the difference in the dimensions of the height of the dose-loading spacer guide and the height of the dose-delivery ring guide for a syringe with inner dimension 4.6 mm and for the loading and delivery of a dose of 7.5 µL was calculated to be 0.45 mm.

Figure 4A:
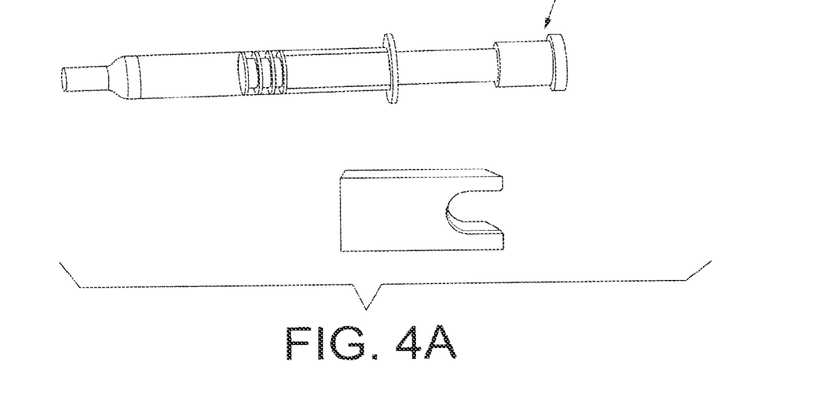
FIG. 4A is a photograph of a syringe bearing an example dose-delivery guide that has been placed on the syringe plunger rod (arrow), and an example removable dose-loading spacer.
Figure 4B:
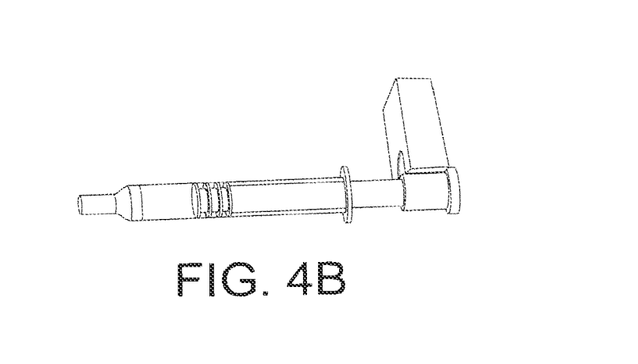
FIG. 4B is a photograph of the syringe of FIG. 4A with the dose-loading spacer placed adjacent to the dose-delivery guide, illustrating how the guides can be configured to fit together.

As can be seen from FIG. 4, the dose-delivery guide can be shaped as a ring or cylinder, or it can have any shape of predetermined dimension. In use, the guide is placed on the syringe, typically at the "top" or proximal end. In the specific example shown in FIG. 4, the guide can be placed around the plunger rod of the syringe (FIG. 4A). In FIG. 4, the dose-delivery guide's inner dimension (I.D.) is slightly larger than the outer dimension (O.D.) of the plunger, such that the guide can move freely along the length of the plunger. In other words, in FIG. 4, the plunger moves through the dose-delivery guide. In the specific embodiment shown in FIG. 4, the dose-delivery guide is a continuous metal "ring," and can be placed on the plunger before the plunger is engaged with the syringe, or before or after the syringe is loaded. Alternatively, the dose-delivery guide may have an opening on the circumference to allow it to deform and "snap on" an extended plunger, substantially surrounding the plunger so that it may be released by the user and maintain its position along the plunger. The dose-delivery guide can be removable or permanent.

The guide can be used without or with the dose-loading spacer described herein. In a particular embodiment, the dose-delivery guide is configured to fit snuggly into the opening of the dose-loading spacer guide (FIG. 4B). Alternatively, the dose-loading spacer is configured to abut either end of the dose-delivery guide.

In use, the dose-delivery guide is placed on the syringe either before or after the syringe is loaded with fluid. The amount of fluid loaded may be determined in traditional fashion (e.g., by visual inspection), without use of a dose-loading spacer. In this circumstance, the dose-delivery guide is advantageous when the syringe is somewhat deformable, such that the dose delivery guide adds stability and thus better control over the dose delivered.

When used with the dose-loading spacer, the dose-delivery guide is placed on the syringe either before or after the syringe is loaded with fluid; the syringe is loaded with excess fluid; the dose-loading guide spacer is placed over/against the dose-delivery guide; the plunger is depressed until the dose-loading spacer stops the motion of the plunger, expelling excess fluid; the dose-loading guide is removed; the syringe needle is placed where the fluid is to be delivered; the plunger is depressed until the dose-delivery guide stops the motion of the plunger, delivering the fluid (e.g., administering the medication). In other words, the plunger travels along the length of the syringe barrel from point A to point B, the distance between point A and B is directly related to the height of the dose-loading spacer and the height of the dose-delivery guide, and related to the volume (dose) to be delivered by the syringe.

Figure 5A:
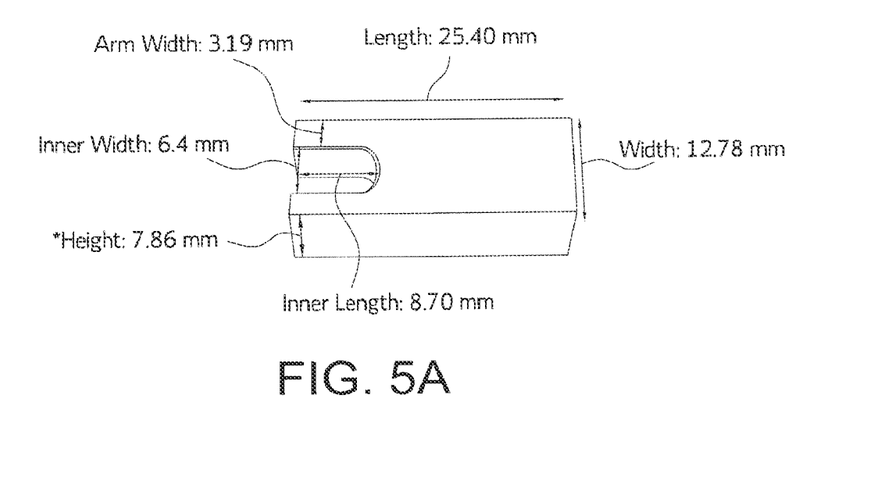
FIGS. 5A and 5B are photographs of example dose-loading and dose-delivery guides with predetermined measurements correlated with the volume to be loaded and delivered. In this embodiment, the dose-delivery guide has a greater length dimension than the dose-loading guide because the syringe flange at the proximal end of the barrel has an indentation that receives the dose-delivery guide to the depth of 0.6 mm. * indicates critical measurement: tolerance should be within ±0.02 mm. ID: inner dimension; OD: outer dimension.
Figure 5B:
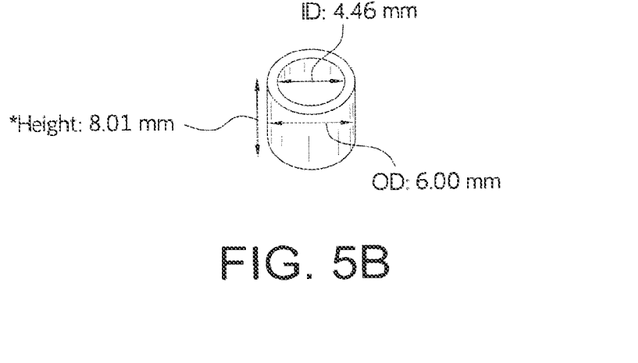

Referring to FIG. 5, this embodiment illustrates a system of a dual dose-loading spacer (FIG. 5A) configured for use with a dose-delivery guide (FIG. 5B). This example was designed for use with a BD 0.5 cc Hypak™ glass syringe with a BD PrecisionGlide™ 27 G ½" needle to deliver a dose of 7.5 µL. In this example, the syringe has a depression at the proximal end in which the dose-delivery guide inserts 0.6 mm. Thus, the dimensions of the dose-delivery guide has a longer height than that of the dose-loading guide, 8.01 mm compared to 7.86 mm spacer, respectively, to account for the depression in the syringe and still guide the accurate delivery of a 7.5 µL dose.

The dose-loading guide, dose-delivery guide, and the dual guide system (dose-loading/dose-delivery guides) of the present invention are particularly useful in circumstances where precise volumes of medication or sample are required. For example, delivery of a precise volume can be important when a pharmaceutical is very active such that a small amount results in significant biological activity (such as insulin); or where a pharmaceutical may have side-effects if a non-precise volume is delivered; or where the site of administration is small, such as in the eye (for example, IBI-20089, IBI-10090, Lucentis® ranibizumab injection, Avastin® bevacizumab, or VEGF Trap-Eye).

The dose-loading guide, dose-delivery guide or dual guide system of the present invention may also be included in a kit. The kit may include at least one guide or dual guide system; or may include a first guide or dual guide system for loading a first dose unit, and a second guide or second dual guide system for loading a second dose unit volume, etc. The kit may include at least one syringe for use with the guide or dual guide system. The kit may include a pharmaceutical or other active agent, a standard (e.g., for use with analytical detection), or materials for user practice (e.g., saline). The pharmaceutical may be preloaded into the syringe, e.g., excess pharmaceutical has been preloaded into the barrel of the syringe.

EXAMPLES

Example 1. Improvement of Small Volume Syringe-Loading Accuracy with Dose-Loading Spacer This example was designed to determine the standard deviation of using a 28 gauge syringe to deliver 7.5 µL of a sustained release composition (IBI-10090, having a density of ~1.15 mg/µL), with or without a dose-loading "spacer" guide.

Four people were given ten commercial insulin syringes (28 gauge); for each syringe, about 10 µL was drawn directly from a sample vial. Excess sample was expressed until approximately 7.5 µL was retained in the syringe as determined visually (i.e., by "eyeballing" the correct unit volume). The unit volume was then injected into a tared vial and the weight recorded. This was repeated for all ten syringes.

The same four people then withdrew about 10 µL of sample and expressed the excess volume with the aid of the removable dose-loading guide as described herein until approximately 7.5 µL was retained in the syringe as determined by the collar portion of the dose-loading guide. The unit volume was then injected into a tared vial and the weight recorded. This was repeated for all ten syringes. The data are shown in Table 1:

TABLE 1

Comparative accuracy of syringe loading, dosing, without or with guide

| | without dose-loading guide | | | | with removable dose-loading guide | | | |
| --- | --- | --- | --- | --- | --- | --- | --- | --- |
| | User | | | | | | | |
| Syringe | 1 (mg) | 2 (mg) | 3 (mg) | 4 (mg) | 1 (mg) | 2 (mg) | 3 (mg) | 4 (mg) |
| 1 | 7.23 | 10.85 | 9.47 | 7.76 | 9.52 | 9.50 | 9.55 | 8.15 |
| 2 | 7.54 | 10.11 | 7.06 | 9.56 | 9.62 | 9.94 | 9.01 | 8.18 |
| 3 | 7.47 | 9.50 | 9.36 | 10.09 | 8.93 | 9.37 | 8.25 | 9.08 |
| 4 | 8.47 | 9.96 | 13.36 | 6.12 | 9.60 | 8.44 | 7.70 | 8.30 |
| 5 | 7.10 | 10.11 | 12.43 | 9.85 | 8.70 | 8.55 | 8.48 | 8.89 |
| 6 | 9.23 | 11.20 | 7.94 | 10.47 | 8.48 | 7.63 | 9.07 | 8.15 |
| 7 | 9.54 | 8.51 | 10.42 | 8.99 | 9.20 | 8.10 | 8.06 | 7.89 |
| 8 | 8.32 | 8.45 | 10.28 | 10.06 | 9.75 | 8.12 | 8.74 | 8.06 |
| 9 | 9.19 | 11.94 | 10.72 | 8.99 | 8.43 | 8.15 | 9.62 | 8.39 |
| 10 | 9.09 | 10.06 | 11.53 | 7.30 | 8.79 | 9.23 | 7.75 | 8.11 |
| | Average weight (mg) 9.39 | | | | Average weight (mg) 8.68 | | | |
| | SD 1.57 | | | | SD 0.63 | | | |
| | RSD 16.68 | | | | RSD 7.28 | | | |
| | Average volume (µL) 8.17 | | | | Average volume (µL) 7.48 | | | |
| | SD 1.36 | | | | SD 0.55 | | | |
| | RSD 16.68 | | | | RSD 7.35 | | | |

As can be seen from the data in Table 1, significant accuracy was achieved by using the dose-loading spacer device.

In several additional experiments using the removable dose-loading guide, syringes were loaded with a pharmaceutical composition using the guide, and accuracy was demonstrated as shown in Table 2:

TABLE 2

| | Accuracy of 300 guided 7.5 μL doses | | | |
|---|---|---|---|---|
| # syringes | # users | Total | ave mg | ave μL |
| 10 | 10 | 100 | 8.72 ± 1.05 | 7.58 ± 0.91 |
| 10 | 10 | 100 | 8.454 ± 0.79 | 7.43 ± 0.69 |
| 10 | 10 | 100 | 8.55 ± 0.68 | 7.50 ± 0.59 |

A further set of data was collected using water, as shown in Table 3:

TABLE 3

| | Accuracy of 100 guided 7.5 μL doses | | | |
|---|---|---|---|---|
| # syringes | # users | Total | ave mg | ave μL |
| 10 | 10 | 100 | 7.53 ± 0.44 | 7.53 ± 0.44 |

Example 2. Dual Dose-Loading/Dose-Delivery Guide System

In early experiments, using a 8.45 mm dose-loading spacer and a 8.00 mm dose-delivery ring with the BD 0.5 cc Hypak™ glass syringe attached with a BD PrecisionGlide™ 27 G ½" needle, the volume delivered was higher than the expected 7.5 μL. After careful examination of the BD Hypak™ syringe, it was found that the flange of the proximal end of the syringe, where the plunger rod enters the syringe barrel, is not perfectly flat; but rather it has a 0.6 mm depression or groove in which the delivery-guide actually seats into or sinks in. The dimensions of the dose-loading guide and the dose-delivery guide were then re-designed to make a 7.85 mm spacer and corresponding 8.0 mm ring, which resulted in the more accurate delivery of a ~7.5 μL dose. Table 4 shows data compiled using this dual guide system for a fluid having a density of 1.16 gm/mL (1.16 mg/μL), such that 8.62 mg/1.16 mg/μL=7.43 μL.

TABLE 4

| | Delivery of 7.5 μL using dual dose-loading dose-delivery guide system | | | | | | | | |
|---|---|---|---|---|---|---|---|---|---|
| | Syringe # | | | | | | | | |
| | 1 | 2 | 3 | 4 | 5 | 6 | 7 | Weight (mg) | Volume (μL) |
| | 9.10 | 8.89 | 8.65 | 8.27 | 8.27 | 9.37 | 8.71 | | |
| | 9.18 | 8.69 | 9.16 | 8.20 | 8.90 | 9.69 | 7.29 | | |
| | 8.55 | 8.22 | 9.17 | 7.98 | 8.57 | 9.99 | 7.91 | | |
| | 8.38 | 8.54 | 8.94 | 8.70 | 8.79 | 8.92 | 8.37 | | |
| | 9.96 | 9.03 | 8.99 | 8.34 | 8.58 | 9.33 | 8.06 | | |
| | 8.44 | 8.35 | 8.62 | 8.32 | 8.67 | 9.20 | 6.89 | | |
| | 8.88 | 8.71 | 9.02 | 8.56 | 8.32 | 8.56 | 7.28 | | |
| | 8.85 | 8.41 | 9.11 | 8.65 | 8.89 | 8.41 | 7.98 | | |
| | 8.97 | 8.08 | 8.44 | 8.20 | 8.79 | 7.93 | 7.87 | | |
| | 9.12 | 8.80 | 8.88 | 8.18 | 8.47 | 9.42 | 8.50 | | |
| Average | 8.94 | 8.57 | 8.90 | 8.34 | 8.63 | 9.08 | 7.89 | 8.62 | 7.43 |
| SD | 0.46 | 0.31 | 0.25 | 0.23 | 0.22 | 0.63 | 0.58 | 0.55 | 0.47 |
| RD | 5.12 | 3.56 | 2.81 | 2.75 | 2.59 | 6.91 | 7.38 | 6.39 | 6.39 |

We claim:

1. A system for delivering a small dose volume from an injection syringe, comprising:

a syringe barrel defining a proximal end and a distal end;

a plunger rod, defining a proximal end and a distal end, slidably disposed within the syringe barrel;

a dose-delivery guide, wherein
the dose-delivery guide is disposed at least partially around the plunger rod,
the dose-delivery guide is disposed adjacent to the proximal end of the syringe barrel,
the dose-delivery guide is rigid along its height,
the dose-delivery guide stops movement of the plunger rod into the syringe barrel at a first predetermined distance defined between the proximal end of the syringe barrel and the distal end of the plunger rod; and a dose-loading guide comprising a grip portion and a collar portion connected to the grip portion, wherein
the grip portion facilitates positioning of the collar portion along the plunger rod during dose loading,
the grip portion facilitates removal of the collar portion after dose loading,
the collar portion is rigid along its height,
the collar portion defines an opening that removably receives the dose-delivery guide during dose-loading, and that is disposed around the dose-delivery guide,
the collar portion stops movement of the plunger rod into the syringe barrel at a second predetermined distance defined between the proximal end of the syringe barrel and the distal end of the plunger rod,
wherein a difference between the first predetermined distance and the second predetermined distance defines a dose volume.

2. The system of claim 1, wherein the second predetermined distance is greater than the first predetermined distance.

3. The system of claim 2, wherein the difference is h, calculated by the formula:

$$h = v/\pi r^2$$

wherein v is the dose volume and r is a radius of the syringe barrel.

4. The system of claim 3, wherein:

v is measured in microliters, r is measured in mm, and h is measured in mm.

5. The system of claim 1, wherein the first predetermined distance is configured to correct for a depression at the proximal end of the syringe barrel.

6. The system of claim 1, wherein the dose-delivery guide is integral to the plunger.

7. The system of claim 1, further comprising a pharmaceutical composition loaded in the injection syringe.

8. The system of claim 7, wherein the pharmaceutical composition is selected from a group consisting of IBI-20089, IBI-10090, ranizumab, bevacizumab, and VEGF Trap-Eye.

9. A system for delivering a small dose volume from an injection syringe, comprising:
- a syringe barrel defining a proximal end and a distal end;
- a plunger rod, defining a proximal end and a distal end, slidably disposed within the syringe barrel;
- a dose-delivery guide, wherein
  - the dose-delivery guide is configured to be disposed at least partially around the plunger rod adjacent to the proximal end of the syringe barrel,
  - the dose-delivery guide is rigid along its height,
  - wherein the dose-delivery guide is configured such that when the dose-delivery guide is disposed around the plunger rod the dose-delivery guide stops movement of the plunger rod into the syringe barrel at a first predetermined distance defined between the proximal end of the syringe barrel and the distal end of the plunger rod; and
- a dose-loading guide comprising a grip portion and a collar portion connected to the grip portion, wherein
  - the grip portion facilitates positioning of the collar portion along the plunger rod in advance of dose loading,
  - the grip portion facilitates removal of the collar portion after dose loading,
  - the collar portion is rigid along its height,
  - the collar portion defines an opening that is configured to removably receive the dose-delivery guide during dose loading,
  - wherein the collar portion is configured such that when the collar portion is disposed around the dose-delivery guide the collar portion stops movement of the plunger rod into the syringe barrel at a second predetermined distance defined between the proximal end of the syringe barrel and the distal end of the plunger rod,
- wherein a difference between the first predetermined distance and the second predetermined distance defines a dose volume.

* * * * *